United States Patent [19]

Moore et al.

[11] Patent Number: 4,497,823

[45] Date of Patent: Feb. 5, 1985

[54] THERAPEUTIC METHOD TO REDUCE PAIN AND INFLAMMATION

[76] Inventors: William T. Moore, Box 76, Old Chimney Farm, Carversville, Pa. 18913; John W. Albright, 7 Pendleton Dr., Cherry Hill, N.J. 08003

[21] Appl. No.: 480,018

[22] Filed: Mar. 29, 1983

Related U.S. Application Data

[63] Continuation-in-part of Ser. No. 439,620, Nov. 5, 1982, abandoned.

[51] Int. Cl.³ .............................................. A61K 31/265
[52] U.S. Cl. ................................. 514/512; 514/825; 514/862; 514/859
[58] Field of Search ........................................ 424/301

Primary Examiner—Stanley J. Friedman
Attorney, Agent, or Firm—Ratner & Prestia

[57] ABSTRACT

Method of treating veterinary or human patients for relief of dermal or sub-dermal pain and inflammation by topical application of a therapeutic agent comprising propylene carbonate.

5 Claims, No Drawings

THERAPEUTIC METHOD TO REDUCE PAIN AND INFLAMMATION

This is a continuation-in-part of U.S. patent application Ser. No. 439,620, filed Nov. 5, 1982, now abandoned.

BACKGROUND OF THE INVENTION

This invention pertains to a new method for treating pain, inflammation, trauma, allergy, and disease by the topical application of a therapeutic agent having previously unrecognized analgesic, anti-allergenic, and anti-inflammatory properties, or by the topical application of the same agent in combination with a second therapeutic agent, the effectiveness of which is enhanced by the first agent.

As stated in the publication of Texaco Chemical Company entitled "Ethylene Carbonate-Propylene Carbonate," "Propylene Carbonate is a clear, mobile, practically odorless liquid." It is 4-methyl 2-dioxolone, a cyclic organic ester which is a known solvent for a variety of polar and non-polar organic compounds and for many inorganic chemical and biological materials. Its chemical properties include low toxicity. The same publication further indicates that propylene carbonate is an excellent additive for certain clays and gel bases useful in cosmetic and personal care products. Still further, the publication refers to acute toxicity tests which indicate that propylene carbonate is practically non-toxic and is otherwise indicated to be non-offensive in subchronic dermal applications, skin sensitization tests and inhalation tests, though temporarily offensive to a minor degree to the eyes.

The Texaco publication also includes a extensive bibliography, including an applications section entitled "Cosmetics and Personal Care," in which four patent references and three literature references are noted.

No indication whatsoever is found in the above-referenced Texaco publication to suggest, in any way, the possible utility of propylene carbonate as a therapeutic agent for treating pain, inflammation, trauma, allergy, or disease.

A search has been conducted in the U.S. Patent and Trademark Office to identify references relating to or disclosing the use of propylene carbonate for essentially any pharmaceutical purpose. Patents identified in this search were:

| U.S. PAT. NO. | INVENTOR |
| --- | --- |
| 4,017,615 | Shastri, et al. |
| 4,279,901 | Ronald M. Kudla |
| 3,924,004 | Chang et al. |
| 4,273,770 | Francisco Alvarez |
| 4,242,334 | Stache et al. |
| 3,829,826 | Gaetano D'Alelio |
| 3,574,118 | Wayne Otto Baker |
| 3,362,927 | Edwin H. Lochridge |
| 3,185,627 | Gus S. Kass |
| 3,178,352 | Roy Erickson |
| 3,136,696 | Benjamin Harrison |
| 3,472,931 | R. B. Stoughton |
| 4,244,942 | Kamishita et al. |
| 3,298,919 | Jack L. Bishop, Jr. |
| 3,352,753 | Leonard J. Lerner |

The first three of the above-listed patents are listed in the Application-Cosmetics and Personal Care subsection of the bibliography in the above-referenced Texaco Chemical Company publication (page 24). The primary focus of Kudla is on ethylene carbonate rather than propylene carbonate. It will also be noted that the remaining references in that bibliography subsection all deal only with hair-treatment preparations. The patents on Chang, Shastri et al., and Kudla all relate to topical ointment compositions in which, generally, propylene carbonate or ethylene carbonate is combined with co-solvents or with other constituents, such that only a minor proportion of propylene carbonate is included in each composition, generally less than 40% in Chang and 30% in Shastri, for example. The compositions, in which propylene carbonate is incorporated in accordance with the teachings of these patents, each include specific therapeutic agents, such as anti-biotics, steroids, antihistamines, antiseptics, anesthetics, and corticosteroids.

The D'Alelio patent relates to the use of propylene carbonate in removing dental calculus, relying on its non-toxic solvent function for swelling the organic binder phase of the calculus.

Alvarez is directed to novel anti-inflammatory agents. It indicates, however, that such agents may be combined with a "pharmaceutically acceptable solvent," among particularly suitable examples of which is listed propylene carbonate. As in other applications of this type, the carbonate is generally carried in a semi-solid emulsion of oil and water, or water in oil including, for example, white petrolatum.

The Stache patent was cited apparently for its teaching of various carbonate-containing steroids useful in veterinary and human therapy. Notably absent, according to Applicants' reading of this patent, is any suggestion of the use of propylene carbonate in any manner different than that suggested in the other prior art references, cited above.

In addition to the foregoing, Applicants are aware of certain unpublished non-clinical work of others. Applicants' limited knowledge of this work prior to the present invention, indicated that propylene carbonate had been considered only for possible use as a rapid surface skin-penetrating carrier for a topically applied composition, namely suntan lotion, the objective of which was to eliminate the greasy surface feel commonly associated with existing suntan lotion. It is not known whether any such suntan lotion was ever prepared.

Notwithstanding prior knowledge of propylene carbonate and its limited use as a vehicle in topical medicaments, and notwithstanding the unpublished work of others suggesting propylene carbonate as a vehicle for suntan lotion, there remains a continuing need for more effective methods of therapy to relieve pain and inflammation and to treat trauma, allergy, and disease. This need has not been addressed in the art pertaining to propylene carbonate.

It is, therefore, the general object of the present invention to provide such a method by the topical application of a hitherto unrecognized therapeutic agent, either alone or in combination with a second agent, the therapeutic effectiveness of which is enhanced by the first agent.

BRIEF DESCRIPTION OF THE INVENTION

The present invention comprises a method to reduce pain and inflammation in surface tissue and in deep or sub-dermal tissue, such as bone, muscle, ligaments, or joints, of a human or veterinary patient by topical application, in the patient's skin or mucous membrane proximate the pain or inflammation, of a therapeutically effective amount of a medicament comprising propylene carbonate. The present invention also comprises a method to treat trauma, allergy or disease by the topical application of propylene carbonate, in combination with a second therapeutic agent appropriate to the trauma or allergy or disease, the effectiveness of which is enhanced by the propylene carbonate.

DETAILED DESCRIPTION OF INVENTION

As contrasted with prior art compositions in which limited amounts of propylene carbonate have been used as a vehicle or carrier for other pharmaceutical agents, the present invention involves a therapeutic method in which propylene carbonate is not merely a vehicle but a primary medicament. While the therapeutic composition used in the method of this invention may include other constituents, either as a stabilizer for the propylene carbonate or as a co-reactive medicament, the present invention has been found effective even in the absence of such stabilizers and co-reactive medicaments.

Thus, in most of the clinical tests described below, the effective therapeutical agent consisted essentially or entirely of propylene carbonate. These tests clearly demonstrate the hitherto unrecognized effectiveness of propylene carbonate as a therapeutic agent. Certain of the tests described below also demonstrate the effectiveness of propylene carbonate as a potentiating agent for a second or co-reactive medicament.

Technical explanations for the surprising results in the clinical tests of the present invention described below are speculative. Accordingly, Applicants do not wish to be bound by any such explanations. However, certain unique characteristics of propylene carbonate seem to be particularly significant.

First, the solvent properties of propylene carbonate are well known. Because of these properties, it has been used or proposed as a vehicle or carrier in a number of topically applied medicinal and cosmetic compositions. These same solvent properties, however, apparently based on the chemical affinity of propylene carbonate for a wide range of other chemical compounds, also make it appropriate as a penetrant. But enhanced penetrating properties due to the propylene carbonate constituent has not been a recognized characteristic of known propylene carbonate-containing medicinal and cosmetic compositions. Applicants now surmise this is because all such compositions include oils, fats, or emulsifiers, in addition to the propylene carbonate. These oils, fats, and emulsifiers are thought to inhibit the penetrating ability and mobility of propylene carbonate. In this respect, the "Comparative Example" discussed below is of interest.

As presently understood then, an important factor in the present invention is the absence, in the topically applied medicament used in this invention, of any penetration inhibiting constituent. This is believed to be important because it apparently enables the propylene carbonate, with its penetrating ability uninhibited, to migrate quickly to the sub-dermal region where its therapeutic value, and/or the therapeutic value of any co-reactive medicament with which it is combined, is expeditiously realized.

A second important characteristic of propylene carbonate, for purposes of the present invention, is thought to be the biological/chemical process by which it degrades through one or more free radical stages to non-toxic final products, namely propylene glycol and carbon dioxide. This may be of significance for two reasons. Primarily, if the final degradation products are innocuous, adverse long range side effects, caused by accumulated by-products, are unlikely. Secondly, the free radical intermediate products, through which propylene carbonate apparently degrades in the body, may function as metabolic accelerators and as nerve cell transmission blockers, resulting respectively in the enhancement of other normal bodily functions dependent on metabolic reactions and in the inhibition of neuro transmission of pain impulses to the brain. The latter may provide symptomatic relief of pain while the former may enhance the normal physiological tendency of a body member to counteract the abnormality, whether it be allergy, inflammation, trauma, or disease.

The accelerated metabolic activity associated with propylene carbonate degradation in the body may also be responsible for the enhanced effectiveness of other co-reactive medications administered in combination with propylene carbonate. For example, the clinical tests described below include several cases in which a solution of propylene carbonate with a co-reactive agent (namely aspirin, iodine, and penicillin, respectively, in separate tests) was used. Positive clinical therapeutic results were obtained in each case. The effectiveness of all three of these medications was apparently enhanced by the presence of propylene carbonate. The apparently improved pharmacologic responses suggest that only a reduced dosage of each medication would be needed in order to produce the desired therapeutic effect. An especially striking example was the case in which a solution of propylene carbonate and penicillin was applied locally to an abcessed tooth and gum (Test 73, below).

In Table I, below, are listed a number of clinical tests in which propylene carbonate was used alone, and in which almost immediate relief from pain, swelling, inflammation, and allergic phenomenon was obtained. Relief from pain usually lasted from 4 to 6 hours which coincides in general with the period of time believed to be required for the degradation of propylene carbonate in the body. In some of the clinical examples, repeated applications of propylene carbonate were necessary in order to obtain relief from pain; in others, prolonged relief was provided after only one application; in still others, continued use of propylene carbonate resulted in prolonged relief as more specifically indicated below. At least, temporary relief from pain, and at best, prolonged remission was obtained by the topical application of propylene carbonate alone. This was especially so in instances where pain and inflammation were associated with joint and muscle trauma, osteoarthritis, bursitis, tendonitis, sprains, hematomas, fractures, torn ligaments and muscles. In those instances where pain returned (although generally lessened) within 4 to 6 hours, repeated application of propylene carbonate seemed to hasten ultimate complete recovery.

TABLE I

| Test Patient Number | Grade & Date of Result | Age | Sex | Ailment | Area of Topical Application | Time to Relieve Pain | Duration of Effect |
|---|---|---|---|---|---|---|---|
| 1. | E - 5/18/82 | 56 | F | Bursitis (Chronic) (mild) | Left Shoulder | 2-3 Min. | 8-10 Hours |
| 2. | G - 3 Applications 5/22/82 5/29/80 6/5/82 | 24 | M | Lower Back Pain (3 Week Duration) | Lumbar & Sacral Regions | 20-25 Min. | 6-8 Hours |
| 3. | E - 3 Applications 5/22/82 5/23/82 5/25/82 | 22 | M | Infected Tooth and Jaw | Skin Over Left Mandibular Region | 2-3 Min. Pain & Swelling Reduced by 2nd Application | 6-8 Hours |
| 4. | E - 3 Applications 5/18/82 5/20/82 5/25/82 | 67 | M | Osteo-Arthritis | Hands & Shoulder | 5 Min. | 4-6 Hours |
| 5. | E - 4 Applications 5/25/82 5/26/82 5/27/82 5/28/82 | 61 | F | Osteo-Arthritis | Hands & Feet | 3 Min. | 4-6 Hours |
| 6. | F - 6/7/82 | 18 | F | Pulled Groin | Left & Right Inguinal Region | 5 Min. - Slight Effect Vague Response | 30 Min. |
| 7. | E - 6/12/82 | 45 | F | Foot Bones Broken Hematoma Right Foot | Ventrum & Dorsum of Foot | Immediate Effect - Complete Relief From Pain | 30 Min. |
| 8. | E - 2 Applications 6/16/82 - AM and PM | 43 | M | Smashed Index Finger (Nail bed) | Index Right Finger | 3-5 Min. Pain Reduced; Moved Finger Freely With No Pain; Healing Hastened | 6-8 Hours |
| 9. | G - 6/16/82 | 16 | F | Osteo-Arthritis - Locked Middle Finger | Middle Finger | Two Applications Needed; Finger Unlocked | |
| 10. | E - 3 Applications 6/19/82 6/20/82 6/21/82 | 31 | F | Abcess Following Tooth Removal Healing Hastened | Skin Over Right Mandible | 5 Min. - Pain Relieved | 6 Hours |
| 11. | N - 6/22/82 | 30 | F | Sprained Wrist | Wrist | Little or No Effect; No Explanation Found; Possibly Psychosomatic Symptoms | |
| 12. | E - 4 Applications 6/24/82 6/25/82 6/26/82 6/27/82 | 38 | F | Osteo-Arthritis of Knees | Both Knees | Within 10 Min. Pain Gone | 10-12 Hours Used as Needed for 2 mo. Period With Continued Relief |
| 13. | E - 2 Applications 6/18/82 AM & PM | 74 | F | Cervical Osteo-Arthritis | Cervical Neck | 30 Min. | 8 Hours |
| 14. | E - 6/22/82 | 20 | F | Sprained Left Ankle | Left Ankle | 2-3 Min. | 8-10 Hours |
| 15. | G - 2 Applications 6/24/82 | 35 | F | (2 Teeth) Right Lower Jaw; Post Wisdom Tooth Extractions | Right Jaw Painful & Swollen | 5 Min. Pain Relieved, also Swelling Seemed Reduced | 8 Hours |
| 16. | E - 6/24/82 | 67 | M | Osteo-Arthritis of Toes | Toes of Left Foot | 2 Min. | 6-8 Hours or Better |
| 17. | E - 3 Applications 6/28/82 6/29/82 6/30/82 | 63 | F | Osteo-Arthritis Left Thumb & Hip | Left Thumb, Hand, & Hip | On Hand 4-5 Min. - On Hip 15-20 Min. | 8-12 Hours Stiffness Down, Mobility Up. After Use for 1 Week Hip Pain Gone - no reapplication needed |
| 18. | G - 2 Applications 7/4/82 | 59 | M | Lower Back Muscle Sprain | Lower Back 2 Appl. | 2-3 Hours | 12 Hours |
| 19. | N 7/5/82 | 45 | M | Lower Back Pain Chronic Intermittent for 10 Years - No Diagnosis | Lower Back 2 Appl. | 1st Appl. No effect. 2nd Appl. 4 Hours Later | 2-3 Min. Slight Improvement Only - No Significant Effect |
| 20. | N - 3 Applications 7/8/82 7/9/82 7/10/82 | 80 | F | Osteo Chronic Back & Legs - 3 Ruptured Lumbar Discs | (Reports are Uncertain) Leg Pain Remained the same. No measurable improvement | | |
| 21. | E - 2 Applications 7/10/82 7/11/82 | 35 | F | Chronic Pain of Severe Scoliosis (Lumbar Region) | Lower Back | 10-15 Min. | 6-8 Hours Continued Use for 6 Weeks, as Needed, Gave |

TABLE I-continued

| Test Patient Number | Grade & Date of Result | Age | Sex | Ailment | Area of Topical Application | Time to Relieve Pain | Duration of Effect |
|---|---|---|---|---|---|---|---|
| 22. | E - 2 Applications 7/13/82 | 27 | F | Acute Tendonitis Right Hand | Right Wrist & Forearm | 10 Min. | Consistent Relief 8 Hours Repeated Applications. Effective over the next week. |
| 23. | E - 7/15/82 | 47 | M | Bursitis Right Wrist Left Shoulder | Wrist & Shoulder | 1-2 Min. | 5-6 Hours |
| 24. | E - 7/15/82 | 61 | F | Osteo-Arthritis Left Knee & Right Ankle | Left Knee & Right Ankle | 5 Min. | 5 Hours |
| 25. | E - 7/16/82 | 60 | F | Osteo-Arthritis Both Hands, Fingers Marked Deformity of Pip Joints | Distal & Proximal Dip & Pip Joints | Stiffness Reduced 5 Min.; also Tenderness Reduced on her Only Tender Joint, Pip Left Small Finger | 4 Hours |
| 26. | F - 7/19/82 | 24 | F | Herneated I.V. Disc (Lumbar) - Later Removed | $L_1$-$L_5$ Area | 10-15 Min. Pain in Back & Muscle Gone - Radiated Pain to Legs Uneffected | 4 Hours |
| 27. | E - 2 Applications 7/19/82 7/20/82 | 56 | F | Cervical Pain & Stiffness in Morning | Cervical 1-8 | Pain Gone in 5 Min. - Refer to #33 | Remainder of Day |
| 28. | F - 7/19/82 | 24 | M | Middle Toe, Right Foot - Arthritis of Undetermined Type | Pip × 2 | Some Numbing of Mild Pain. Had taken Indocin that A.M. - Test Invalid | For 1 Week Afterwards Toe was Mobile at Joint Where it was Previously Fixed. |
| 29. | G - 7/24/82 | 50 | M | Lower Back Lumbo-Sacral | Lumbo-Sacral Region | Pain Relief in 10 Min. | 5-6 Hours |
| 30. | E - 7/28/82 | 86 | F | Osteo-Arthritis Knees | Knees (P.C. With Aspirin) | Pain Relief ½ Hour | 4 Hours |
| 31. | Lidex Ointment Compared with 100% Propylene Carbonate | | | | | | |
| a. | N - Lidex 6/19/82 | 61 | F | Osteo-Arthritis | Left Hand Lidex | No Reaction | 100% P.C. Applied Over Lidex - Still No Reaction in Left Hand |
| b. | E - 100% P.C. 6/19/82 | | | | Right Hand Propylene Carbonate Only | 2-3 Min. | 4-6 Hours |
| 32. | N - 5/20/82 | 70 | F | Osteo-Arthritis | Hands Several Appl. | No Effect | Discovered That Water had Contaminated P.C. |
| 33. | N - 7/25/82 | 56 | F | Cervical Pain & Stiffness Same Pt. as #27 | *1st Appl. effect Lasted Only 10 Min. 2nd Appl. 2-3 Min. for Effect With Fresh P.C. | | 4 Hours |
| 34. | E - 7/30/82 | 63 | F | Osteo-Arthritis Hip, Knee & Ankle | Applied P.R.N. for 6 wks. | Less P.C. Needed and Quicker Response After Repeated Use | |

*Note: Suspect first application failed due to contamination of propylene carbonate.

| Test Patient Number | Grade & Date of Result | Age | Sex | Ailment | Area of Topical Application | Time to Relieve Pain | Duration of Effect |
|---|---|---|---|---|---|---|---|
| 35. | E - 7/30/82 | 38 | F | Night Cramps in Legs (Calf) | To Calves of Legs | 20 Min. | For the Night. No Awakening from Cramps |
| 36. | N to F - 8/5/82 8/13/82 P.C. 8/13/82 P.C.A.* | 69 | M | Rheumatoid Arthritis Hands, Hip, & Leg | Hands Daily for 1 Week. P.C.A. - After 2 Days - Less Stiff Swelling Less, Mild Relief - No Significant Improvement | P.C. - No Relief; Used 2 Times | |
| 37. | E - 8/13/82 | 27 | F | $T_{11}$ & $T_{12}$ Severe Sprain Intercostal Pain - Rear to Front | $T_{11}$ & $T_{12}$ & Dermatome | 10 Min. Relief | Back Improved After One Application |

TABLE I-continued

| Test Patient Number | Grade & Date of Result | Age | Sex | Ailment | Area of Topical Application | Time to Relieve Pain | Duration of Effect |
|---|---|---|---|---|---|---|---|
| 38. | E - 8/15/82 | 56 | F | Lower Back Pain Sacrum | Lower Back | 20 Min. No Pain | Several Applications Over Period of 2 Weeks; Relief Each Time |
| 39. | G - 8/23/82 | 16 | M | Trauma to Right Wrist & Forearm Swollen & Painful | Fracture of Radius & Ulna Applied to Wrist & Forearm | 10-20 Min. Swelling Down Pain Diminished on Forearm. Wrist Slightly Numbed | |
| 40. | G - 9/3/82 | 59 | M | Hematoma on Right Forearm Result of Trauma | To Hematoma | Within 1½ Hour | Swelling Reduced, Pain Diminished |
| 41. | E - 9/15/82 | 16 | M | Trauma Left Forefinger, Jammed Swollen Finger & Hand, Severe Pain | To Left Forefinger & Hand | 2-5 Min. | Pain Relieved; Swelling Reduced in within ½ Hour. Finger Freely Movable Without Pain or Limitation |
| | | | | Also Right Scapula & Trapezius Muscle Traumatized Echymosis & Hematoma | To Skin over Right | 2-5 Min. | Pain Completely Relieved - Freedom of Movement Without Pain |
| 42. | E - 10/2/82 | 56 | M | Tennis Elbow Right | To Right Elbow | 3-5 Min. | Pain Relieved for 4-5 Hours |
| 43. | E - 10/11/82 | 56 | F | Back Sprain | To Lumbar-Sacral Region | 10-20 Min. | Pain Relieved Remainder of Day |
| 44. | F - 10/16/82 | 44 | M | T2-Rib Broken With Referred Pain | To Fracture Area and T2 Dermatome | Within 5 Min. the Referred Pain Was Absent Movement on Site of Fracture Pain Confined though Reduced | Effective ½ Hour |
| 45. | E - 10/17/82 | 67 | M | Hemiplegia-Stroke, Pain in Arm & Leg | To Painful Arm & Leg | 5-10 Min. | Relieves Pain 4-5 Hrs. Used Daily for 6-8 Weeks |
| 46. | E - 11/3/82 | 56 | F | Bursitis Rt. Shoulder | 1 Application at Bedtime | 5 Min. | No Pain No Limited Motion the Next Morning |
| 47. | E - 11/4/82 | 16 | M | Knee Trauma Rt. Knee Football | 1 Application to Rt. Knee | 10-15 Min. Pain Reduced Swelling Down | No Return of Pain Or Swelling the Next Day |
| 48. | E - 11/10/82 | 32 | F | "Joggers" Knee Pain | 1 Application to Affected Knee | Pain Diminished in 2-3 Min. Absent After ½ Hour | No Return of Pain the Next Day |
| 49. | E - 11/16/82 | 50 | F | Sprained Ankle (Rt.) | 1 Application | Pain Gone in 10-15 Min. Swelling Reduced | No Return That Day Slightly Tender Next Day. PC Reapplied, No Return of Pain Rest of Day |
| 50. | E - 11/22/82 | 54 | F | Unremitting Pain from Osteo-Arthritic Knees for 3½ yrs. | Applied to the Knees | Within 10 Min. Pain Remitted | No Return of Pain Rest of Day |
| 51. | E - 11/21/82 11/22/82 11/23/82 | 24 | F | 1 Yr. Ago Broken Ankle (left) Pinned, Chronic Swelling & Pain for 1 Yr. | Applied to Painful Ankle on 3 Different Days | Swelling Relieved in 2-3 Min. | Pain Disappeared for the Entire Day on Each of the 3 Days |
| 52. | G - 11/25/82 | 23 | F | Trauma to Lt. Small Toe. Swollen Purple & Painful | Lt. Small Toe 2 Applications 3 Hrs. Apart | 3-5 Min. | First Application - Pain and Swelling Reduced. After 3 hrs., Some Swelling & Pain Returned. Second Application - Reduced Pain & Swelling |
| 53. | E - 11/27/82 | 22 | M | L3, L4, & L5 Torn Tendons Lt. Lat. Dorsal MM Torn Ligament. Bed-fast 3 Days | Left Side L3, L4, & L5, also Insertions of Lt. Lat. Dorsal MM. | 15 Min. Pain Diminished | 1 Hr. - Pain Gone, no Return of Pain or MM Spasm; Patient was Up and Around |
| 54. | E - 11/28/82 | 51 | F | Post Oper. - 4 wks. | On Incisional | 10 Min. | Pain Gone in 10 |

TABLE I-continued

| Test Patient Number | Grade & Date of Result | Age | Sex | Ailment | Area of Topical Application | Time to Relieve Pain | Duration of Effect |
|---|---|---|---|---|---|---|---|
| | | | | Hysterectomy Incision Pain on Incision & Bilateral Inguinal Ligament & Inner Thighs | Scar, Inguinal Regions & Inner Thighs | | Min. with Return in 8 hrs.; then Pain was Greatly Reduced |
| 55. | E - 11/29 through 12/12/82 | 27 | F | Fractured Lt. Clavicle Painful & Swollen. PC used Several ×/day for 2 wks. | Applied Directly Over Swelling | 10 Min. Pain Reduced | Only Slight Tenderness Remained Over the Fracture; Pain Reduced More After Each Application |
| 56. | G - 12/7/82 | 59 | M | Toothache Throbbing Pain | Gum Area Surrounding Tooth | | After 3rd. Application in a Period of 2 Hrs. Pain was Gone |
| 57. | E - 12/7/82 12/8/82 12/9/82 | 33 | F | Sprained Back MM. Rt. Side Previous Episode Took 2 wks. to Heal | Lumbo-Sacral Region & Insertion of Rt. Lat. Dors. MM. Applied 2-3 times Daily for 3 days | | Response Good; Pain Diminished First Day. Back Improved From Each Application |
| 58. | E - 12/20/82 | 38 | M | Lower Back Sprain (Lifted Garage Door); wore a back brace | Sprayed Entire Lumbo-Sacral Region of the back | 10 Min. | 10 Min. Pain Reduced. 20 Min. Pain Gone and Brace not Needed When Patient Walked Out |
| 59. | E - 12/28/82 12/29/82 12/20/82 | 44 | M | Lower Back Pain | Lower Back Over Painful Area | 2-3 Min. | Relief Within Minutes; Used Over the Period of 4 Days With Good Results |

GRADING KEY
54 E - Excellent, no pain or awareness at all during period
9 G - Good, relief from pain but an awareness of the area
5 F - Fair, relief from pain is not as definitive nor as striking as Excellent or Good
6 N - None, no change
*Propylene carbonate with aspirin (15% solution)

In addition, a number of dermatologic conditions have been treated, as reported below in Table II (Tests 60–70 and 74) with propylene carbonate alone and with propylene carbonate in combination with a second therapeutic agent.

Test 73 involved treatment of a specific tooth and gum condition in a manner to demonstrate specifically the potentiating effect of propylene carbonate in combination with penicillin.

TABLE II

| Test Patient Number | Test Grade | Age | Sex | Condition | Treatment | Days Used | Improvement Time & Degree |
|---|---|---|---|---|---|---|---|
| 60. | E | 60 | F | Poison Ivy on Both Arms | PC Application to One Arm; Control Arm Not Treated | July 26 Applied Several Days 27th & 28th | Poison Ivy on Arm to Which PC was Applied Cleared up Rapidly. Untreated Arm Did Not Heal. Untreated Arm Showed Discolored Scars; PC Treated Arm no Discoloration, no Scars |
| 61. | E | 17 | M | Acne, Chin & Cheeks; Condomes, Pustules | P.C.I. (Polypylene Carbonate-Iodine, 1000 PPM) Applied 2-3 Times Daily | 8/1/82, 7 days | Pustules Gone in 1 Day; Condomes Reduced in 2 Days; Face Cleared in 5 Days. PCI Continued 1 mo. - Acne Cleared. 1 wk. Without Medication - Acne Returned; with Medication, Face Again Cleared Up |
| 62. | E | 67 | M | Forehead, Rash Allergy | 2 Applications PC | 8/17, 1 day | Itch Gone in Several Hours. Dermatitis Improved Within Hours, Even Though it had Grown Worse for Several Days Prior to Treatment |
| 63. | E | 47 | F | Poison Ivy of Both Legs | 2 Applications Rt. Leg - PC Lt. Leg - PCI (1000 PPM) | 8/17, PC Worked as Well as PCI | 1st Day, PC, Itch Gone Immediately; Redness Gone PCI - Itch Gone Immediately; Redness Gone 2 Days Following; Poison Ivy Dried up on Both Legs; no Discoloration, no Scars |
| 64. | E | 21 | M | Poison Ivy of the Right leg | 2 Applications Rt. Leg - PC | 8/26 | 1st Day Itch Relieved Immediately; Lesions Dried up and Spreading of Poison ivy Prevented |
| 65. | E | 35 | F | Herpes Simplex I of Lips & | Initially 2 Applications | 9/1 & 9/2 & 9/3 | Herpes Simplex Dried up; Lesions Cleared up; |

TABLE II-continued

| Test Patient Number | Test Grade | Age | Sex | Condition | Treatment | Days Used | Improvement Time & Degree |
|---|---|---|---|---|---|---|---|
| | | | | Face; Prior Treatment With Lidex Ineffective | - PC; then PC for 2 Subsequent days | 3 Days | Compared to Lidex Which Had no Effect |
| 66. | E | 24 | F | Acne Vulgaris of Forehead, Cheeks & Chin Moderate | Daily Applications for 3 Months; Beginning on 9/4 - PCI (1000 PPM) | 9/4 through October, November; Used Daily | Improvement Noted on Second Day of PCI Use; Within One Week, Acne Was Almost Cleared |
| 67. | E | 26 | F | Acne Vulgaris Moderate | 2 Times Daily; PCI (2000 PPM) | 10/14, November, December, 1982 | Improvement Began in a Few Days and in Two Weeks Cleared Up |
| 68. | E | 59 | M | First Degree Burn Rt. Index Finger | Only one Application PC | 11/1/82 | Reduced Pain Immediately. Within 2 Hours, There Were No Redness, No Swelling, and No Tenderness - no evidence of burn at all |
| 69. | E | 20 | F | Herpes Simplex of Lip - PC | 2 Applications Daily | 11/8, 11/9 & 11/10/82 | Herpes Lesions Dried Up First Day. Healed in 2-3 Days (By Comparison, Previous Bouts of Herpes Lasted 10 Days to 2 Weeks in this patient) |
| 70. | E | 27 | F | Acne Vulgaris Mild Case | 2 Applications Daily - PCI (2000 PPM) | 11/29/82 - 12/12/82 | Cleared Redness in 1 wk. Papules & Condomes Gone in 2 wks. Then Continued Use as Needed |
| 71. | E | 60 | M | First Degree Burn of Thumb | Immediate Application then 2 times Within One Hour - PC | 12/24/82 | Pain Stopped Immediately; Redness Diminished. There was no Pain and the Formation of Vessicle was Retarded |
| 72. | E | 20 | M | Acne Vulgaris | P.C.I. (2000 PPM) Applied Daily | December through January After a Test Period 7 Days | Marked Improvement First 7 Days. Then on Medication for 6 Weeks, Cleared Completely |
| 73. | Treatment of Pyorrhea of the gum and abscessed gum and molar tooth | | | | | | |
| 74. | E | 25 | F | Infected Ulcerations Dorsum Rt. Foot of 2 wks. Duration | Applied 2 Times for 3 Days - PC; Previous Treatment with A & D Ointment and Furacin were to no Avail | 12/24-25-26/82 | First the Ulcers Dried Up Then Swelling, Pain, and Redness Diminished; by the Third Day, Ulcers Were Dried Up and Healed |

73. Treatment of Pyorrhea of the gum and abscessed gum and molar tooth
  (1) First treatment - Oral Tetracycline 250 mgm. b.i.d. for 15 days
      No improvement of condition
  (2) Second treatment - Oral SKF Pen VK 250 mgm. b.i.d. for 10 days
      No improvement of condition
  (3) Third treatment - Local topical application b.i.d. of ¼ Tab. 250 mgm. of SKF VK in aqueous sol. (dist. H$_2$O) for 7 days
      No improvement of condition
  (4) Fourth Treatment - PC local topical application b.i.d. for 7 days
      Reduced suppuration and bleeding
      Slight improvement - yet condition flared up during two day period without any medication
  (5) Fifth treatment regime - Solution ¼ of a 250 mgm. tablet of Pen VK in solution with PC applied topically to tooth & gum b.i.d. for 7 days.
      Suppuration and swelling completely reduced. Only slight amount of bleeding remained - no flare up during two day rest period without medication
  (6) Sixth treatment regime - a repeat of 2 and 5 in combination, i.e., P.C. & Pen VK (¼ Tab. 250 mgm.) topically b.i.d. plus Pen VK 250 orally b.i.d. for 7 days.
      Abcess healed - no reoccurrence after one month. (i.e., December 31, 1982)

In general, the variety of clinical applications in which propylene carbonate has been tested and found to be useful include: as an anti-inflammatory, an anti-allergenic, a carrier of other therapeutic agents, and as a potentiating agent for other therapeutic agents. The types of co-reactive therapeutic agents with which propylene carbonate has been used include analgesics (e.g., aspirin), antibiotics (e.g., penicillin), and anti-septics (e.g., iodine). Other possible co-reactive medicaments include steroids, cortico-steriods, and anti-histamines.

In addition, the unusual effectiveness (i.e., quick remission) on virus infections and allergic manifestations noted to date suggests that propylene carbonate may have some special effects on histaminic and immunologic systems in the body, thereby, presaging an even wider spectrum of medical applications for this compound.

Among dermatologic and trauma-related conditions which may be treated with propylene carbonate, either alone or in combination with other drugs, are eczemas, burns, lesions, abrasions, incisions, allergies, and infectious disorders such as herpes, scabies, or even psoriatic conditions.

The results of Test 73 indicate that propylene carbonate, in combination with penicillin, is aparently more effective in the treatment of an abscessed tooth and gum (to cause remission of the infectious condition) than either penicillin or propylene carbonate alone. This occurred after the abscess remained resistant to systemic treatment with Tetracycline and SKF Pen VK penicillin. Upon topical application of a solution of propylene carbonate and Pen VK, the abscess showed signs of remission within a week. Upon a second application a week later in conjunction with systemic penicillin treatment, complete remission of the infection resulted.

The results of the other tests reported in Table II may be summarized as follows:

POISON IVY. Upon topical application of propylene carbonate, the poison ivy infected area dried in the same day and was prevented from spreading to other areas. Itching stopped within minutes; the condition healed within a few days without leaving the skin discoloration usually seen as a post-poison ivy condition. This also suggests that propylene carbonate, when applied to other types of lesions of the skin, may accelerate healing and help to minimize scarring.

HERPES SIMPLEX-1 (viral infection). Upon topical application of propylene carbonate to the affected skin area, healing occurred within a few days and did not spread to contiguous areas. Itching stopped immediately and the condition healed within a few days rather than in the usual 7 to 10 days, which occurs without treatment. This suggests the possible efficacy of the use of propylene carbonate in the treatment of the lesions of genital herpes, and the use of propylene carbonate in treating other virus-related conditions.

URTICARIA. Upon the topical application of propylene carbonate to urticaria of the face, the allergic manifestation disappeared within a few hours, apparently acting as an antihistamine.

BURNS. Propylene carbonate was applied topically to first degree burns; pain was immediately relieved, and blistering was prevented. Healing occurred within 2 days.

INFECTED SKIN ULCERATIONS. Upon topical treatment with propylene carbonate the condition healed over a period of 3 days with minimal scarring noted 3 weeks after healing. This condition had been resistant to healing with A & D ointment & Furacin for 2 weeks prior to the use of propylene carbonate.

ACNE VULGARIS (seven cases). By topical application of a solution of 1000 PPM Iodine in propylene carbonate or 2000 PPM Iodine in propylene carbonate, the Acne conditions showed considerable to complete remission. These clinical examples demonstrate the ability of propylene carbonate in combination with a second therapeutic agent, to act as a potentiator as well as a vehicle for that agent.

COMPARATIVE EXAMPLE

The only known medicament listed in the *Physicians' Desk Reference* (Medical Economics Company, Inc., Oradell, NJ: 1982) which includes propylene carbonate is Lidex Ointment, manufactured and sold by Syntex, Inc. of Palo Alto, CA, the apparent assignee of the above-referenced Chang, Shastri, and Alvarez patents. According to the 1982 *Physicians' Desk Reference,* and the literature distributed with Lidex Ointment, it is composed of "Fluocinonide 0.5 mg/g, in a specially formulated ointment based consisting of Amerchol Cab (mixture of sterols and higher alcohols), white petrolatum, propylene carbonate, and propylene glycol. It provides the occlusive and emollient effects desirable in an ointment. In these formulations, the active ingredient is totally in solution." It is said to be effective in the relief of inflammatory manifestations of corticosteroid-responsive dermatoses.

For purposes of comparison with the present invention, Lidex Ointment was topically administered to test case #31-A 61 year old female with osteoarthritis of the hands (Test #31 in Table I above). No relief from the pain occurred when Lidex Ointment was applied to her left hand. Simultaneously, propylene carbonate was applied to her right hand resulting in immediate relief from pain. Additionally, when 100% propylene carbonate was applied over the Lidex Ointment on the left hand, no relief from the pain was obtained presumably because propylene carbonate could not penetrate the Lidex Ointment.

Thereafter, this same patient was made the subject of a clinical test of the present invention, with good results as indicated in Test #31b of Table I.

This significantly better result, obtained using the present invention, is considered to be a dramatic demonstration of the efficacy of the present invention. Moreover, this result is in sharp contrast to the result obtained using a composition, apparently typical of the prior art, in which propylene carbonate is present only in a minor amount and in combination with other solvents, vehicles, and medicaments.

While this invention has been described with reference to specific embodiments thereof, the appended claims are intended to be construed to extend not only to these embodiments and forms of the invention but to such other forms and embodiments as may be devised by those skilled in the art, without departing from the true spirit and scope of the invention.

We claim:

1. A method of treating pain, infection, trauma, or inflammation in the dermal or sub-dermal tissue of a subject by topical administration to the skin area proximate said tissue of a therapeutically effective amount of a medicament consisting essentially of propylene carbonate.

2. A method, as recited in claim 1, wherein osteoarthritis is treated.

3. The method of claim 1 wherein the pain is from abnormal conditions selected from the group consisting of osteo arthritis and related conditions, injury, trauma, allergenic inflammation, poison ivy, tooth and gum abscess, burns, acne or pyorrhea.

4. The method of claim 3 wherein the pain is from osteo arthritis and related conditions.

5. The method of treating pain comprising topical administration to the skin area proximate the pain of a therapeutically effective amount of propylene carbonate.

* * * * *